US012575758B2

(12) United States Patent
Günther et al.

(10) Patent No.: US 12,575,758 B2
(45) Date of Patent: Mar. 17, 2026

(54) SYSTEM FOR DETECTION OF RESPIRATORY GAS COMPONENTS

(71) Applicant: CORTEX Biophysik GmbH, Leipzig (DE)

(72) Inventors: Andreas Günther, Leipzig (DE); Lukas Kulisch, Naunhof (DE)

(73) Assignee: CORTEX Biophysik GmbH, Leipzig (DE)

( * ) Notice: Subject to any disclaimer, the term of this patent is extended or adjusted under 35 U.S.C. 154(b) by 397 days.

(21) Appl. No.: 18/143,145

(22) Filed: May 4, 2023

(65) Prior Publication Data

US 2023/0355131 A1 Nov. 9, 2023

(30) Foreign Application Priority Data

May 4, 2022 (DE) ..................... 10 2022 111 059.1

(51) Int. Cl.
*A61B 5/083* (2006.01)

(52) U.S. Cl.
CPC .... *A61B 5/0836* (2013.01); *A61B 2560/0223* (2013.01)

(58) Field of Classification Search
CPC ..................... A61B 5/0836; A61B 2560/0223
See application file for complete search history.

(56) References Cited

U.S. PATENT DOCUMENTS 5,386,833 A * 2/1995 Uhen .................. A61B 5/0836
600/538
2021/0072225 A1 3/2021 Reinstaedtler

FOREIGN PATENT DOCUMENTS

DE 102014004765 B3 * 7/2015 .......... G01N 33/497
DE 102014204625 A1 * 9/2015 ............ G01N 21/61
DE 102021111431 A1 * 12/2021 .......... A61B 5/0816

* cited by examiner

*Primary Examiner* — Eric F Winakur

(57) ABSTRACT

The present invention relates to a system (100) for detecting respiratory gas components, comprising
a respiratory gas inlet (101),
a measuring cell (103) connected to the respiratory gas inlet (101) with at least one respiratory gas sensor,
a gas outlet (105) downstream of the measuring cell (103),
a data processing unit connected to the measuring cell (103),
an energy supply (107),
characterized in that the system (100) has an additional sensor (109) for measuring at least the carbon dioxide content of the ambient air of the system (100).

11 Claims, 4 Drawing Sheets

SYSTEM FOR DETECTION OF RESPIRATORY GAS COMPONENTS

Figure 1:
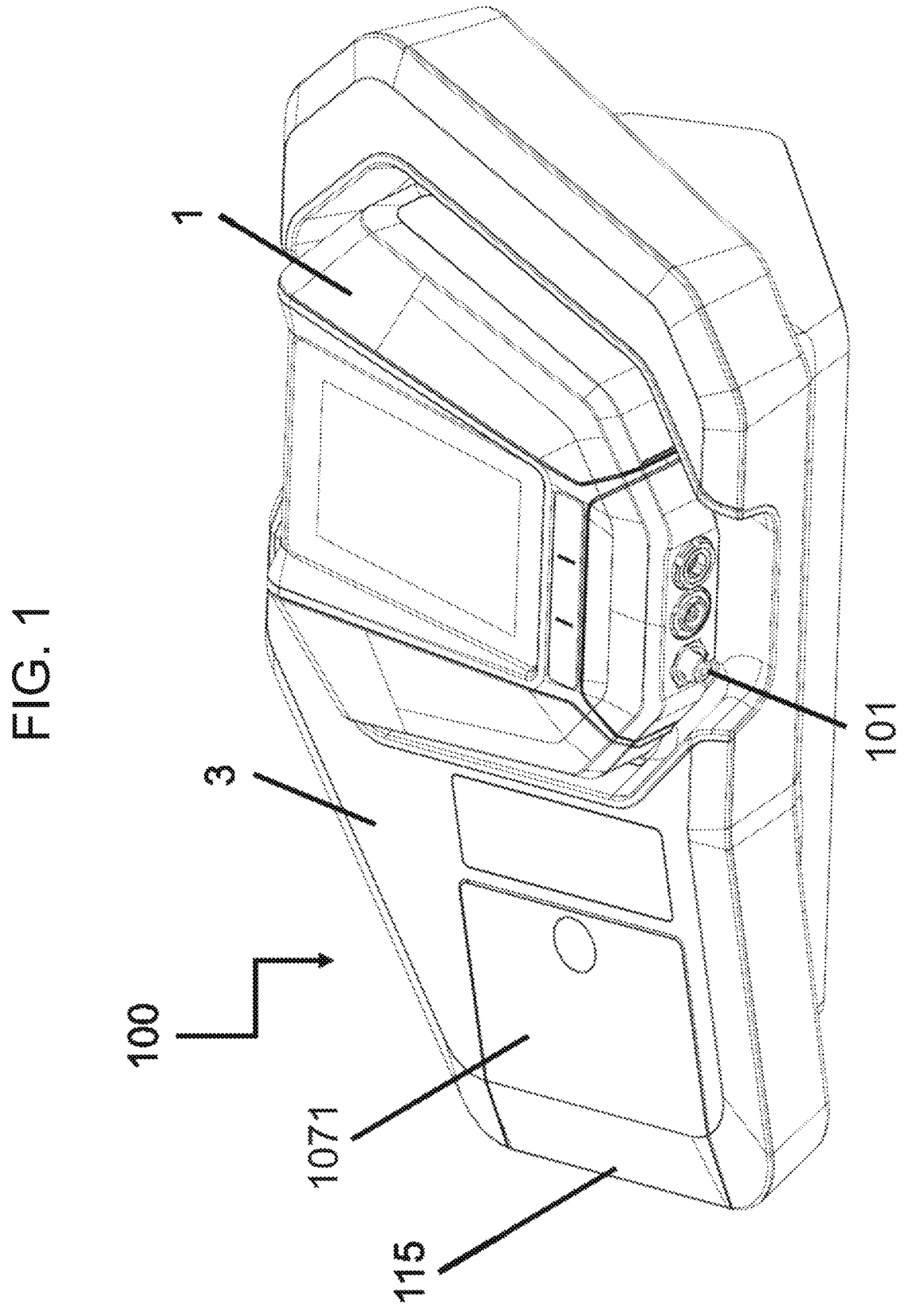

The invention deals with a system for detecting respiratory gas components, which can be used, in particular, in spiroergometry.

In the diagnostic procedure of spiroergometry (also known as ergospirometry or ergospirography), the heart reactions, blood circulation, breathing, metabolism, and/or cardiopulmonary performance are qualitatively and quantitatively examined by measuring respiratory gases during physical stress.

Spiroergometry devices are therefore designed as high-precision medical measuring instruments. The respective device must have an outstanding measuring accuracy. Due to inherent factors (e.g. ageing, consumption) and external influences (e.g. temperature fluctuations), the characteristic curves of the sensors used in the spiroergometry devices may change. This means that they cannot maintain the required measurement accuracy over a long period of time. Therefore, the measurement deviation (calibration) must be determined at regular intervals and the measurement signal must be accordingly adjusted. Thus, calibration/adjustment significantly facilitates to ensure that the measurement results of spiroergometry devices meet the requirements of established standards of spiroergometry and market requirements.

Usually two gas analysis sensors are used in spiroergometry equipment, an oxygen sensor ($O_2$ sensor) and a carbon dioxide sensor ($CO_2$ sensor).

The oxygen's sensor characteristic curve is strongly influenced by temperature, as the respective chemical reaction can be faster or slower, depending on the thermal influence. In addition, the chemical reactants are consumed like in a battery. As a result, the longer the oxygen sensor is used the weaker the output signal. Thus conventional oxygen sensors rarely feature a real long-term stability.

For example, the carbon dioxide sensor uses the near-infrared absorption spectrum. Carbon dioxide molecules absorb infrared light of a very specific wavelength. The carbon dioxide sensor consists of an infrared source and a detector for exactly the wavelength required. The sensor characteristic curve is determined by heat radiation coming from the outside and the ageing of the infrared light source.

Due to the above-mentioned influences, both curve slope and displacement change in the characteristic curves of the two sensors (oxygen and carbon dioxide).

In order to shift the characteristic curve of the two sensors at the zero point, as well as to adjust the rise of this characteristic curve, two exact reference measuring points are required. The two-point calibration (or two-point adjustment) method is currently state of the art. A reference measuring point is usually a test gas (or calibration gas), whose composition imitates the expiratory air of humans (15 vol.-% $O_2$, 5 vol.-% $CO_2$, the rest is $N_2$). The test gas is technically manufactured with sufficient accuracy. The second reference point is the ambient air, which refers to the inspired air. For fresh air, a solid composition of 20.93 vol.-% $O_2$ and 0.035 vol.-% $CO_2$ (the rest is mainly $N_2$) is assumed. In closed rooms and laboratories, however, the ambient air composition may strongly vary because of people's presence in the room.

In addition, in clinical facilities and laboratories it is not always possible to open the window and to aerate the room. Sometimes it is done by fixed ventilation systems installed specially for this purpose. However, nobody knows how well such systems work and supply fresh air. In such cases, fresh air is taken as the second reference measuring point, although it is not exactly known what the latter really consists of. Thus you have to put up with a measurement error.

This measurement error can be several percent, depending on how much the real gas composition in the room deviates from the fresh air values taken as a basis. In closed and poorly aerated rooms, carbon dioxide concentration is often even 0.4 vol.-% and higher. In exceptional cases, even levels above 1 vol.-% may occur.

In view of the problems described above, there is a great need to at least minimize, if not completely prevent, the measurement errors occurring during ambient air calibration because of unknown ambient air composition.

So far, traditional approaches could not meet this need satisfactorily. For example, it was suggested to use a $CO_2$ absorber (e.g. soda lime) in the device, which absorbs $CO_2$ from the ambient air and thus generates a reference point with 0 vol.-% $CO_2$. Alternatively, a second test gas with a composition comparable to fresh air can be kept in a replaceable calibration gas cylinder in the device. Because both options require certain consumables, the calibration/adjustment becomes just more complicated without actually meeting the requirements described above.

Other approaches require $O_2$ sensors to determine the actual 02 content in the ambient air. However, this approach entails a problem. The oxygen sensors featuring appropriate sensitivity and measurement accuracy do not provide long-term stability and need to be regularly calibrated or replaced themselves. The calibration would then need to be done again, for example, with additional test gases, which does not create any added value to the current state of the art.

The purpose of the present invention is therefore to provide a novel uncomplicated and handling-efficient system for detecting respiratory gas components, which minimizes the measurement errors occurring during calibration to the ambient air. Another purpose of the invention is to inform the user about the current $CO_2$ content in the room in order to initiate appropriate countermeasures in advance of performance measurements (room ventilation).

In the present invention these two aims are achieved by a system (100) for detecting respiratory gas components, which comprises a respiratory gas inlet (101), a measuring cell (103) connected to the respiratory gas inlet (101) with at least one respiratory gas sensor, a gas outlet (105) downstream of the measuring cell (103), a data processing unit connected to the measuring cell (103), an energy supply (107), characterized by the feature that the system (100) has an additional sensor (109) for measuring at least the carbon dioxide content of the system's (100) ambient air.

In the present invention "respiratory gas inlet" means a port to which a hose is connected for the system's (100) use, which leads to a breathing mask of the subject.

In the invention, the "measuring cell" (103) is an arrangement of respiratory gas sensors (usually an oxygen and a carbon dioxide sensor) and a measuring unit for the flow rate detection (e.g. a differential pressure sensor), which are pneumatically connected in series and are passed through by the respiratory gas extracted from the breathing mask. All elements of the "measuring cell" (103) are connected to a data processing unit, in particular in the form of a microcontroller.

The "gas outlet" ensures that the measured respiratory gases are discharged from the system (100).

According to the invention, the power supply (107) can be, for example, a mains connection and/or a battery unit.

The characteristic feature of the inventive system (100) is an additional sensor (109) for measuring at least the carbon dioxide content of the ambient air of the system (100). By measuring the actual $CO_2$ concentration in the ambient air (carbon dioxide content), instead of using standard theoretical concentration values ($O_2$: 20.93 vol.-%; $CO_2$: 0.035 vol.-%), the respiratory gas sensors of the measuring cell (103) can be accurately calibrated not simply on the basis of theoretical values. Thereby, the disadvantages of the prior state of the art are overcome. Therefore, this sensor can be considered a separate "reference sensor" for calibration based on the actual $CO_2$ concentration in the ambient air.

The additional sensor (109) is specially designed to measure only the carbon dioxide content in the ambient air of the system (100). This can therefore be regarded as a separate "reference sensor" for calibrating the respiratory gas sensors of the measuring cell (103) on the basis of the determined $CO_2$ concentration.

Generally, the advantage of the present invention is that an exact measurement of the actual $CO_2$ concentration in the ambient air can be made with the inventive system (100) in order to minimize the error in the calibration of the respiratory gas sensors of the measuring cell (103) in the system (100).

Unlike the prior state of the art, for this inventive solution, no consumables ($CO_2$ absorbers, test gas, etc.) are necessary. Furthermore, the additional sensor (109) used according to the invention is of a small design and can thus also be integrated into a compact and portable device. This combination of features also enables automatic two-point calibration.

In addition, it is possible to provide users/subjects with information about the current $CO_2$ content in the room. In this way, appropriate countermeasures such as room ventilation can be taken in advance of the performance measurements planned.

Further development envisages that the additional sensor (109) is designed for optimized calibration of the respiratory gas sensors of the measuring cell (103) on the basis of the actual carbon dioxide content in the ambient air of the system (100).

In contrast to the known prior state of the art, the invention does not assume the standard composition with a fixed $CO_2$ concentration (usually 0.035 vol.-%) for the ambient air, but determines the actual $CO_2$ concentration in the ambient air and uses this value as a basis for calibration of the respiratory gas sensor. This prevents the systematic measurement errors occurring in the case of the prior state of the art, as described above. After calibration of the respiratory gas sensor with the actual $CO_2$ concentration, a correct and reliable measurement of the respiratory gas components can be performed.

For implementation of the present invention, it turned out to be advantageous to use the additional sensor (109), which at least measures the carbon dioxide content, as a low-calibration sensor with high long-term stability. The sensor used in the invention has a calibration interval of 5 years and is otherwise largely maintenance-free. However, since this calibration also demands much effort from the user (use of calibration gas, etc.), the sensor used according to the invention can be simply replaced by an exchangeable compartment after 5 years.

In contrast to the known oxygen sensors, which usually provide no long-term stability and must be regularly adjusted or replaced, the system (100) provided in the present invention is low-maintenance, at least with regard to the exchange unit (111) with integrated additional sensor (109) for measuring at least the carbon dioxide content, and can be used safely and sensibly even by non-trained users/test persons without any problems.

Another inventive embodiment of the system (100) provides that the additional sensor (109) for measuring only the carbon dioxide content features a measuring accuracy of at least ±50 ppm+3%.

In the application of the inventive system (100) for spiroergometry, even small changes in the gas concentrations in the ambient air (a few ppm) significantly influence the measurement results, if calibration is based on theoretical standard concentrations. However, in the current state of the art, no oxygen sensors are known that can steadily measure such small changes in $O_2$ concentration in a room and/or over a long period of time without need to be calibrated themselves. The oxygen sensors theoretically applicable for this purpose and detecting ambient air are too large to be integrated into compact and portable devices. Moreover, these oxygen sensors require much maintenance. Thus, in the case of oxygen ambient sensors the specialist will face difficult technical obstacles.

In the present invention it was worked out that conversion of $O_2$ concentrations measured by the method of a prior state of the art into $CO_2$ concentrations is basically possible in order to then calibrate a respiratory gas sensor. This is because the oxygen amount consumed by a human ($VO_2$) is converted into an equivalent volume of carbon dioxide ($VCO_2$). For example, if the $O_2$ percentage in a room falls by 0.5% by volume, the $CO_2$ percentage will increase by 0.5% by volume-%.

With the additional sensor (109) used according to the invention, not only the $CO_2$ respiratory gas sensor of the measuring cell (103) can be calibrated with the actual $CO_2$ content in the ambient air. Moreover, the $O_2$ respiratory gas sensor of the measuring cell (103) is calibrated by recalculating the measured $CO_2$ content to the actual $O_2$ content in the ambient air.

A totally exact equivalent conversion is not possible, because due to diverse metabolic processes in the human body (e.g. mixture of fat & carbohydrate combustion) no fully equivalent conversion possible. Nevertheless, the resulting error is smaller than the error that would occur without taking into account any room air change.

In a preferred embodiment of the inventive system (100), the additional sensor (109) for measuring at least the carbon dioxide content is arranged in an externally accessible exchange unit (111), whose positioning on the inventive system (100) is also designed to screen the additional sensor (109) from respiratory gas components.

Based on the state of the art, calibration intervals of up to five years are specified for $CO_2$ sensors for indoor air monitoring. Within this period, manufacturers assure that the $CO_2$ sensors comply with the specified measurement accuracy (e.g. of ±50 ppm+3% of the measured value). Such long-term stability is not known in conventional oxygen sensors. Since the inventive system (100) is designed for a lifetime of at least ten years, the $CO_2$ sensor must be either recalibrable or replaceable. The effort required from a user (consumer or non-specialist) for recalibration is very high due to the open design of most of the available $CO_2$ sensors and entail the major problem of incorrect calibration. According to the invention, this additional high effort should be avoided For this reason, in the present invention the $CO_2$ sensor (109) is designed so that the user can replace it by the externally accessible exchange unit (111) in the system (100).

The exchange unit (111) accessible from outside is located in particular on the rear side of the system, i.e. on the side away from the user, in order to screen it from the exhale air. In this way, the $CO_2$ sensor (109) used as a reference (and thus the calibration) is not affected by the normal breathing of the user. In addition, attached to the rear, the exchange unit (111) and the $CO_2$ sensor (109) protected from influence by unwanted contact usually occurring during use of the system (100).

Moreover, an advantageous further development of the inventive system (100) is equipped with a unit (113) for active gas exchange with the ambient air. This device (113) may be designed as a pneumatic hose system with a solenoid valve as the core component. This also allows faster changes in the carbon dioxide content of the ambient air to be precisely recorded.

This further development is designed to quickly and accurately detect changes in $CO_2$ concentration in a room. Passive ventilation based on pure convection would only allow a slow exchange with the ambient air. Therefore, detection of rapid changes in indoor air quality is delayed. For this purpose, in the invention, the additional sensor (109) is intensively flooded with the ambient air, firstly by providing a plurality of ventilation holes in the exchange unit's (111) housing, and secondly by means of the device (113), through which the ambient air to be measured is sucked directly through the exchange unit (111) during calibration.

For the most practical and easy use of the inventive system (100), it proved to be advantageous to equip it with a fully automatic calibration unit. The active gas extraction of the ambient air required for the $CO_2$ measurement described above can be extended to a fully automatic calibration by connecting a test gas cylinder to the system (100). During the two-point calibration, the device (113) switches between the ambient air and the test gas.

In another preferred embodiment of the inventive system (100), the power supply (107) has battery cells (1071) in at least one externally accessible exchangeable compartment (115).

In this case, the battery cells (1071) can be arranged redundantly, so that empty/used battery cells (1071) can be replaced while at the same time still charged battery cells (1071) ensure the energy supply. In this way, there is no need to interrupt the inventive system (100) use.

The inventive system (100) is designed in a special further development with a mobile device (1) and a stationary unit (3) in two parts, wherein the mobile device (1) comprises the respiratory gas inlet (101), the measuring cell (103) with at least one respiratory gas sensor, the gas outlet (105) and the data processing unit together with a separate energy unit (117), wherein the stationary device (3) is designed for reversible reception of the mobile device (1).

This special further development of the present invention combines advantages of a mobile device (1) in terms of variability and mobility with advantages of a stationary unit (3) provided with features that cannot be accommodated in a mobile device (1), as far as comfortability and easy handling is required for mobile use by test subjects.

In this case, the additional sensor (109) characterizing the inventive system (100) and measuring at least the carbon dioxide content in the ambient air is arranged in the stationary device (3), since this is normally installed in closed rooms. In contrast, the mobile device (1) is generally used outdoors, where fresh air can be assumed as ambient air with the above-mentioned oxygen and carbon dioxide contents.

If various features not required for mobile measurement are transferred into the stationary device (3), the mobile device (1) can be made very small and comfortable for mobile use.

For the special further development of the present invention, it was found to be advantageous that both the mobile device (1) and the stationary unit (3) have mechanical snap-in connections (119a, 119b) for releasable, force-locking connection and a data interface (121) for connection to each other.

At first, this ensures that the mobile device (1) is not accidentally removed from the stationary unit (3) or falls down. Furthermore, the mechanical snap-in connection (119a, 119b) ensures a correct connection of the data interface (121).

In the special further development of the present invention, the mobile device (1) can also be used without any problems when the user moves (e.g. during outdoor sports). For such cases, the mobile device (1) is preferably provided with a mechanical snap-lock (119c) for releasable force-locking connecting to a body carrier system (5). This mechanical snap-lock (119c) may preferably be identical to the mechanical snap-lock (119b) for connection to the stationary unit (3).

According to the special further development of the present invention, the inventive system (100) has also an advantage that the mobile device (1) does not exceed a dimension of 15.6 cm×16.2 cm×4.8 cm. Thanks to this compactness, the mobile device (1) does not disturb the user even during his movement and can be used in particular with the appropriate body carrier system (5), largely without restrictions on mobility. In the current state of the art no spiroergometry mobile devices are known which have comparable technical characteristics and such small dimensions at the same time.

The small dimensions of the mobile device (1) are possible, in particular, since in this invention the features required outdoors and in closed rooms are separated depending on the intended use. In this way, the two-part system (100) of this particular embodiment can not only realize all the advantages described above, but also provides maximum variability in its use.

In a second aspect of the present invention, the included system (100) as described above is designed for use in spiroergometry, spirometry, and measurement of metabolic rates at rest.

Figure 2:
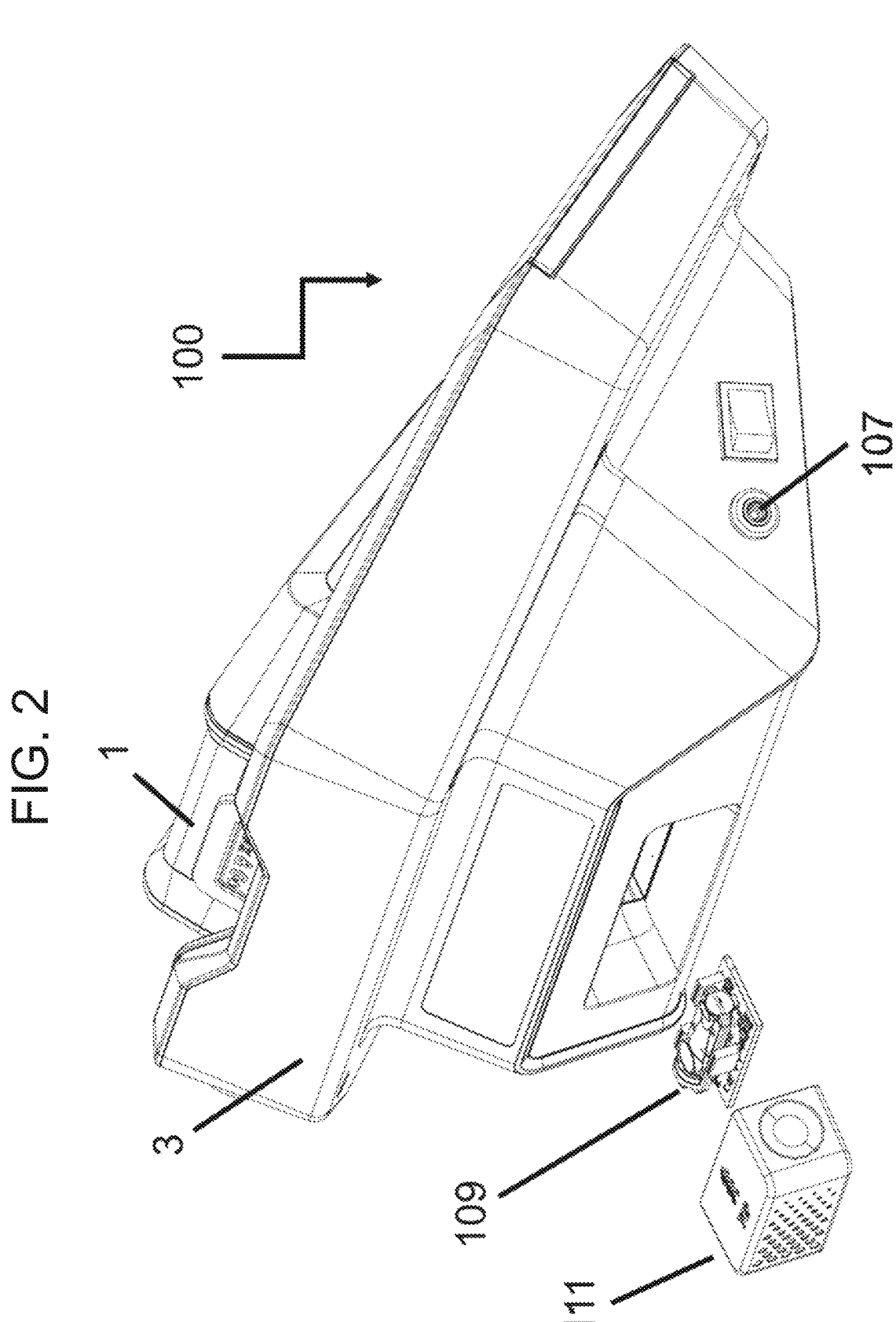
Figure 3:
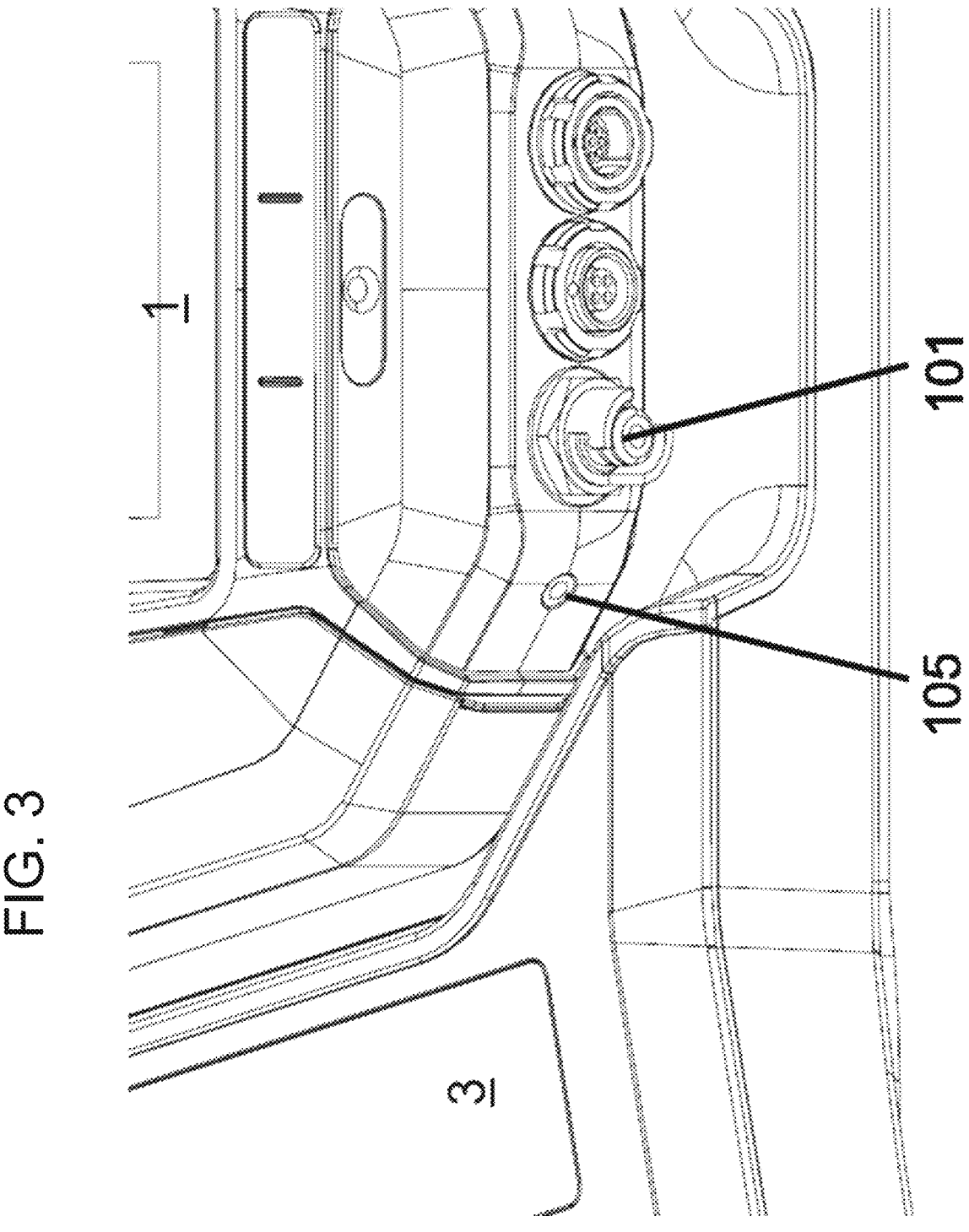
Figure 4:

Further objectives, features, advantages and possible applications are derived from the following description of embodiments that do not restrict the invention, also with reference to the figures. In this case, all the described and/or pictorially illustrated features, in isolation or in any combination, constitute the subject matter of the invention, even irrespective of their summary in the claims or their referring. Illustrations show, as follows:

FIG. 1 a graphical representation of the inventive system 100 in a preferred embodiment, FIG. 2 a graphical representation of the inventive system 100 in FIG. 1 in a rear side view, FIG. 3 a graphical detailed representation of the inventive system 100 in FIG. 1, FIG. 4 a block diagram of the inventive system 100 in a preferred embodiment.

In the figures, all the same components are named with the same reference marks, but for more clarity, not all reference characters are necessarily inserted in all representations.

In FIG. 1 the inventive system 100 is graphically represented as an entire system in a preferred embodiment. This preferred embodiment is based on the two-part design with mobile device 1 and stationary unit 3. Mobile device 1 is designed as a mobile measuring device that can be removed from the system 100 for measurements in field.

Moreover, FIG. 1 shows arrangement of the externally accessible exchangeable compartment 115, in which the battery cells 1071 are placed. On the front of the system 100, specifically on the mobile device 1 there are various ports, in particular, respiratory gas inlet 101.

FIG. 2 shows a graphic representation of the inventive system 100 of FIG. 1 in a rear view seen from the side. It is clearly visible that the $CO_2$ sensor 109 and the replacement unit 111 are arranged on the rear side to prevent contact with the exhalation gas or to avoid accidental touching contacts during the system use. In addition, the power supply port 107 is marked.

The externally accessible changing unit 111 is inserted into the receiving cavity not provided with a reference mark. Thereby, $CO_2$ sensor 109 is placed in its interior. The openings for the ambient air in changing unit 111 are easy to recognize. At the same time largely prevent any other contamination.

FIG. 3 is a detailed graphical representation of various clearly visible connections, including, in particular, respiratory gas inlet 101 and gas outlet 105 downstream of measuring cell 103 that is not shown in the Figure.

Finally, FIG. 4 shows a block diagram of the inventive system 100 in a preferred embodiment described here. The individual components have already been described above or can be taken from the block diagram in a self-explanatory manner. In particular, the selected view shows the individual line systems and connections that are divided between the pneumatic system with internal pneumatic interfaces, the electrical connections with the electrical interfaces and the mechanical connections with the mechanical interfaces.

REFERENCE MARKS LIST 1 mobile device
100 system for detecting respiratory gas components
101 respiratory gas inlet
103 measuring cell
105 gas outlet
107 Energy supply
1071 battery cells
109 additional sensor/$CO_2$ sensor
111 exchangeable unit
113 active gas exchange facility
115 exchangeable compartment
117 energy unit
119a 119b snap-in connection
121 data interface
3 stationary unit
5 body carrier system

The invention claimed is:

1. System for detecting respiratory gas components, comprising
   a respiratory gas inlet,
   a measuring cell connected to the respiratory gas inlet with at least one respiratory gas sensor,
   a gas outlet downstream of the measuring cell,
   a data processing unit connected to the measuring cell,
   an energy supply,
characterized in that the system has an additional sensor for measuring at least the carbon dioxide content of the ambient air of the system;
wherein the additional sensor is designed for measuring only the carbon dioxide content in the ambient air of the system; and
wherein the data processing unit is designed for optimized calibration of the respiratory gas sensors of the measuring cell on the basis of the carbon dioxide content in the ambient air of the system.

2. System according to claim 1, wherein the additional sensor for measuring only the carbon dioxide content is a low-calibration sensor with high long-term stability.

3. System according to claim 1, wherein the additional sensor for measuring only the carbon dioxide content has at least a measuring accuracy of ±50 ppm+3%.

4. System according to claim 1, wherein the additional sensor for measuring only the carbon dioxide content is arranged in an externally accessible exchange unit, whose positioning on the inventive system is designed to screen the additional sensor from respiratory gas components.

5. System according to claim 1, further including a device for active gas exchange with the ambient air.

6. System according to claim 1, further comprising a fully automatic calibration unit.

7. System according to claim 1, wherein the power supply has battery cells in at least one externally accessible exchangeable compartment.

8. System according to claim 1, the system further including a mobile device and a stationary unit,
   wherein the mobile device comprises the respiratory gas inlet, the measuring cell with at least one respiratory gas sensor, the gas outlet and the data processing unit together with a separate energy unit,
   wherein a stationary device is designed for reversible reception of the mobile device.

9. System according to claim 8 wherein the mobile device and the stationary unit each have a mechanical snap-in connection for releasable, force-locking connection and a data interface for connection to each other.

10. System according to claim 8 wherein the mobile device is also provided with a mechanical snap-lock for releasable force-locking connecting to a body carrier system.

11. System according to claim 8 wherein the mobile device does not exceed a dimension of 15.6 cm×16.2 cm×4.8 cm.

* * * * *